US011058896B2

(12) United States Patent
Maltz et al.

(10) Patent No.: US 11,058,896 B2
(45) Date of Patent: Jul. 13, 2021

(54) DEVICES AND METHODS FOR MEASURING A RADIATION OUTPUT RATE AND MONITORING BEAM ENERGY

(71) Applicant: SHANGHAI UNITED IMAGING HEALTHCARE CO., LTD., Shanghai (CN)

(72) Inventors: Jonathan Maltz, Walnut Creek, CA (US); Walter Aguilar, Walnut Creek, CA (US)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

(21) Appl. No.: 16/870,953

(22) Filed: May 9, 2020

(65) Prior Publication Data

US 2020/0269070 A1 Aug. 27, 2020

Related U.S. Application Data

(63) Continuation of application No. 15/909,969, filed on Mar. 1, 2018, now Pat. No. 10,668,303.

(51) Int. Cl.
*A61N 5/10* (2006.01)

(52) U.S. Cl.
CPC ......... *A61N 5/1067* (2013.01); *A61N 5/1071* (2013.01); *A61N 2005/1074* (2013.01)

(58) Field of Classification Search
None
See application file for complete search history.

(56) References Cited

U.S. PATENT DOCUMENTS

2007/0018117 A1* 1/2007 Calderon ............... G01N 23/04
250/492.1
2012/0305790 A1 12/2012 Hanawa et al.
(Continued)

FOREIGN PATENT DOCUMENTS

CN 107648749 A 2/2018
CN 108051845 A 5/2018
(Continued)

OTHER PUBLICATIONS

L Bartol et al., SU-D-BRCD-03: Spectroscopic Characterization of a 6 MV Linear Accelerator Field Using Compton Spectrometry Measurements and Monte Carlo Techniques, Medical Physics, 39(6Part3): 3613, 2012.
(Continued)

*Primary Examiner* — Hoon K Song
(74) *Attorney, Agent, or Firm* — Metis IP LLC

(57) ABSTRACT

A radiation treatment device may include a first dosimeter and a second dosimeter. Quantum efficiency of the first dosimeter may be lower than quantum efficiency of the second dosimeter. A method for monitoring beam energy may include receiving a first signal generated by a first dosimeter, receiving a second signal generated by a second dosimeter, receiving a third signal generated by the first dosimeter and receiving a fourth signal generated by the second dosimeter. The first signal and the second signal may be associated with a first radiation beam. The second signal and the fourth signal may be associated with a second radiation beam. The method may also include determining whether there is a difference between the beam energy of the first radiation beam and the second radiation beam based on at least one of the first signal, the second signal, the third signal or the fourth signal.

20 Claims, 10 Drawing Sheets

(56) References Cited

U.S. PATENT DOCUMENTS

| | | | |
|---|---|---|---|
| 2015/0224343 A1* | 8/2015 | Couture | G01T 1/2018 250/370.07 |
| 2015/0374324 A1* | 12/2015 | Nishimura | A61N 5/1075 600/1 |
| 2016/0121139 A1 | 5/2016 | Da Silva Rodrigues et al. | |
| 2018/0038970 A1 | 2/2018 | Li et al. | |
| 2018/0185673 A1* | 7/2018 | Lee | G21K 5/04 |
| 2019/0175945 A1 | 6/2019 | Yan et al. | |

FOREIGN PATENT DOCUMENTS

| | | | |
|---|---|---|---|
| EP | 2030650 | A2 | 3/2009 |
| EP | 2520335 | A1 | 11/2012 |
| EP | 3015133 | A1 | 5/2016 |
| WO | 0216965 | A2 | 2/2002 |

OTHER PUBLICATIONS

Nils Reims etal., Developing a Compton Spectrometer for Determination of X-ray Tube Spectra, 2012 IEEE Nuclear Science Symposiwn and Medical Imaging Conference Record (NSS/MIC), 3265-3268, 2012.

First Office Action in Chinese Application No. 201910157630.2 dated Jul. 3, 2020, 19 pages.

Zhang Shaogang, Measurement of Normal Dose in Radiotherapy (1) Measurement of Absorbed Dose and Dose Calibration of Medical Accelerator, Chinese Journal of Medical Device, 22(4): 1-10, 2009.

* cited by examiner

600

700

```
┌─────────────────────────────────────────────────────────────┐
│ Receiving a first signal generated by a first dosimeter, the first │
│ signal corresponding to a first radiation output rate of a first   │  ~ 702
│ radiation beam, wherein the first radiation beam is generated at a │
│ first time point by a radiation source                              │
└─────────────────────────────────────────────────────────────┘
                              │
                              ▼
┌─────────────────────────────────────────────────────────────┐
│ Receiving a second signal generated by a second dosimeter, the     │
│ second signal corresponding to at least one of a second radiation  │  ~ 704
│ output rate of the first radiation beam or a first energy spectrum │
│ of the first radiation beam                                         │
└─────────────────────────────────────────────────────────────┘
                              │
                              ▼
┌─────────────────────────────────────────────────────────────┐
│ Receiving a third signal generated by the first dosimeter, the third│
│ signal corresponding to a third radiation output rate of a second  │  ~ 706
│ radiation beam, wherein the second radiation beam is generated at  │
│ a second time point by the radiation source                        │
└─────────────────────────────────────────────────────────────┘
                              │
                              ▼
┌─────────────────────────────────────────────────────────────┐
│ Receiving a fourth signal generated by the second dosimeter, the   │
│ fourth signal corresponding to at least one of a fourth radiation  │  ~ 708
│ output rate of the second radiation beam or a second energy        │
│ spectrum of the second radiation beam                              │
└─────────────────────────────────────────────────────────────┘
                              │
                              ▼
┌─────────────────────────────────────────────────────────────┐
│ Determining, whether there is a difference between the beam        │
│ energy of the first radiation beam and the beam energy of the     │  ~ 710
│ second radiation beam based on at least one of the first signal,   │
│ the second signal, the third signal or the fourth signal           │
└─────────────────────────────────────────────────────────────┘
```

FIG. 7

DEVICES AND METHODS FOR MEASURING A RADIATION OUTPUT RATE AND MONITORING BEAM ENERGY

CROSS-REFERENCE TO RELATED APPLICATIONS

This application is a continuation of U.S. application Ser. No. 15/909,969, filed on Mar. 1, 2018, the entire contents of which are hereby incorporated by reference.

TECHNICAL FIELD

The present disclosure generally relates to radiation therapy, and more particularly, to devices and methods for measuring a radiation output rate and monitoring beam energy in radiation therapy or an imaging process.

BACKGROUND

Radiation treatment has been widely used for clinical treatment for several decades. An imaging process is often required for the radiation treatment. For example, image-guided radiation therapy (IGRT) involves obtaining an image by a scanning operation to direct radiation treatment. The imaging process may also generate images as a record of treatment. Radiation output for imaging is usually much lower than radiation output for a treatment. The same dosimeter may be used to measure the radiation output for the imaging and the radiation output for the treatment. Such a dosimeter may be designed to pass as much radiation as possible and may thus exhibit low quantum efficiency. As a result, the dosimeter may have a limited ability to measure radiation output for imaging operations. Knowledge of the radiation output per imaging frame is important both for recording the imaging dose and for the normalization of an image intensity to the radiation output for the imaging. This is particularly important for computed tomography, in which severe image artifacts may result if the projection images are produced by a variable and unknown amount of radiation per image. The conventional radiation detector used for measuring radiation output by the therapy/imaging system has, by itself, limited ability to detect changes in beam energy. A secondary radiation detector may be used to improve safety, by detecting changes in beam energy (quality) and provide a means of calibrating radiation beam energy spectral characteristics. Therefore, it may be desirable to develop devices and methods for measuring the radiation output rate and monitoring beam energy more accurately and more precisely for radiation therapy or an imaging process.

SUMMARY

According to an aspect of the present disclosure, a radiation treatment device is provided. The radiation treatment device may comprise a radiation source, a first dosimeter, and a second dosimeter. The radiation source may be configured to generate a radiation beam. The first dosimeter may be configured to generate a first signal upon receiving at least portion of the radiation beam. The second dosimeter may be configured to generate a second signal upon receiving at least portion of the radiation beam. The quantum efficiency of the first dosimeter may be lower than quantum efficiency of the second dosimeter.

In some embodiments, the second dosimeter may include an optical detector and a scintillator coupled to the optical detector.

In some embodiments, the optical detector may include a photodiode.

In some embodiments, the scintillator may include a phosphor.

In some embodiments, the scintillator may include a Gd2O2S phosphor.

In some embodiments, the optical detector may include a photomultiplier, and the scintillator may include a cadmium telluride scintillator.

In some embodiments, the photomultiplier may include a silicon photomultiplier.

In some embodiments, the radiation treatment device may further comprise a collimator configured to delimit an extent of the first radiation beam or the second radiation beam. The second dosimeter may be located between the radiation source and the collimator.

In some embodiments, the second dosimeter may be placed so as not to block a radiation-beam-passing-through area between the radiation source and the collimator.

In some embodiments, the second dosimeter may be placed on a moveable component.

In some embodiments, the radiation treatment device may further comprise a backscatter plate located distal, along the beam path, to the first dosimeter. The second dosimeter may be located on the backscatter plate.

In some embodiments, the radiation treatment device may further comprise a carrousel located between the radiation source and the first dosimeter.

The second dosimeter may be located on the carrousel.

In some embodiments, the at least portion of the radiation beam received by the second dosimeter may be scattered from the radiation beam.

In some embodiments, the at least portion of the radiation beam received by the second dosimeter may be scattered by a block located beyond a radiation-beam-passing-through area from a first angle.

In some embodiments, the radiation source may be further configured to generate a first radiation beam in a first mode and a second radiation beam in a second mode. The energy level of the second radiation beam may be lower than the energy level of the first radiation beam. The first dosimeter may be further configured to receive at least portion of the first radiation beam under the first mode. The second dosimeter may be further configured to receive at least portion of the second radiation beam under the second mode.

In some embodiments, the first mode may be a treatment mode.

In some embodiments, the second mode may be an imaging mode or a calibration mode.

According to another aspect of the present disclosure, a method for monitoring beam energy is provided. The method may be implemented on a computing device having at least one processor and a non-transitory storage medium. The method may include receiving a first signal generated by a first dosimeter. The first signal may correspond to a first radiation output rate of a first radiation beam. The first radiation beam may be generated at a first time point by a radiation source. The method may also include receiving a second signal generated by a second dosimeter. The second signal may correspond to at least one of a second radiation output rate of the first radiation beam or a first energy spectrum of the first radiation beam. The method may also include receiving a third signal generated by the first dosimeter. The third signal may correspond to a third radiation output rate of a second radiation beam. The second radiation beam may be generated at a second time point by the radiation source. The method may also include receiving a fourth signal generated by the second dosimeter. The fourth signal may correspond to at least one of a fourth radiation output rate of the second radiation beam or a second energy spectrum of the second radiation beam. The method may also include determining whether there is a difference between the beam energy of the first radiation beam and the beam energy of the second radiation beam based on at least one of the first signal, the second signal, the third signal or the fourth signal.

In some embodiments, quantum efficiency of the first dosimeter may be lower than quantum efficiency of the second dosimeter.

In some embodiments, determining whether there is a difference between the beam energy of the first radiation beam and the beam energy of the second radiation beam may further include determining a first relationship between the first signal and the second signal. The method may also include determining a second relationship between the third signal and the fourth signal. The method may also include determining whether there is a difference between the first relationship and the second relationship. In response to the determination that there is the difference between the first relationship and the second relationship, the method may include determining that there is a difference in the beam energy of the first radiation beam and the second radiation beam.

In some embodiments, determining whether there is a difference between the beam energy of the first radiation beam and the beam energy of the second radiation beam may further include determining maximum energy of the first energy spectrum based on the second signal. The method may also include determining maximum energy of the second energy spectrum based on the fourth signal. The method may also include determining whether there is a difference between the maximum energy of the first energy spectrum and the maximum energy of the second energy spectrum. In response to the determination that there is the difference between the maximum energy of the first spectrum and the maximum energy of the second spectrum, the method may include determining that there is the difference between the beam energy of the first radiation beam and the beam energy of the second radiation beam.

According to yet another aspect of the present disclosure, a method for monitoring beam energy is provided. The method may be implemented on a computing device having at least one processor and a non-transitory storage medium. The method may include receiving a first signal generated by a first dosimeter. The first signal may correspond to a first radiation output rate of a radiation beam. The method may also include receiving a second signal generated by a second dosimeter. The second signal may correspond to a second radiation output rate of the radiation beam. The method may also include determining a relationship between the first signal and the second signal. A difference between the relationship and a reference value may be determined.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 7 is a flowchart illustrating an exemplary process for measuring the radiation output rate and for monitoring beam energy according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 3:
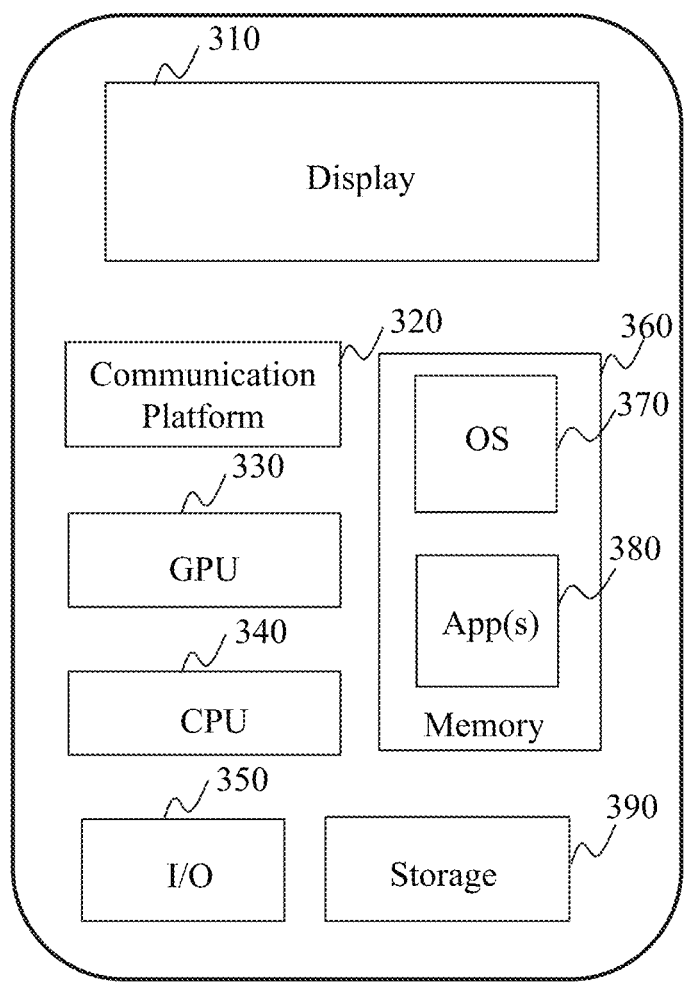
FIG. 3 is a schematic diagram illustrating exemplary hardware and/or software components of an exemplary mobile device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 3) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for medical diagnostic and/or treatment. In some embodiments, the medical system may include an diagnostic system. The diagnostic system may include a multi-modality imaging system. The multi-modality imaging system may include, for example, a computed tomography-positron emission tomography (CT-PET) system, a computed tomography-positron emission tomography-magnetic resonance imaging (CT-MRI) system, a X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a digital subtraction angiography-magnetic resonance imaging (DSA-MRI) system, or the like, or a combination thereof. In some embodiments, the medical system may include a diagnostic and treatment system. The diagnostic and treatment system may include a treatment plan system (TPS), an IGRT system, etc. Merely by way of example, the IGRT system may include, for example, an CT guided radiotherapy system, an MRI guided radiotherapy system, etc.

The present disclosure generally relates to a radiation therapy (RT) system, particularly to RT systems with imaging capabilities. Provided herein are mechanisms (which can include methods, devices, systems, computer-readable medium, etc.) for measuring the radiation output rate and monitoring beam energy. A radiation treatment device is provided, including a first dosimeter and a second dosimeter. The quantum efficiency of the first dosimeter may be lower than the second dosimeter. The first dosimeter may be configured to detect the radiation output rate of a radiation beam, while the second dosimeter may be configured to detect the radiation output rate or an energy spectrum of the radiation beam. The second dosimeter may be positioned to receive primary or scattered radiation. For instance, the second dosimeter may be positioned on an edge of a backscatter plate (Many RT systems include a backscatter plate distal along the beam path to the primary radiation monitor, to shield that monitor from backscatter from the beam collimator system.). The second dosimeter may include an optical detector, and a scintillator connected to the optical detector, for example, a photodiode optically-coupled to a $Gd_2O_2S$ phosphor, a photomultiplier optically-coupled to a cadmium telluride scintillator.

A method for measuring a radiation output rate and monitor beam energy is also provided. The method may be implemented on a processor. The processor may receive a first signal generated by the first dosimeter and a third signal generated by the first dosimeter, wherein the first signal corresponds to a first radiation output rate of a first radiation beam generated at a first time point, and the third signal corresponds to a third radiation output rate of a second radiation beam generated at a second time point. The processor may receive a second signal generated by the second dosimeter and a fourth signal generated by the second dosimeter, wherein the second signal corresponds to at least one of a second radiation output rate of the first radiation beam or a first energy spectrum of the first radiation beam, and the fourth signal corresponds to at least one of a fourth radiation output rate of the second radiation beam or a second energy spectrum of the second radiation beam. In some embodiments, the processor may determine a first relationship between the first signal and the second signal, and determine a second relationship between the third signal and the fourth signal. If there is a difference between the first relationship and the second relationship, the processor may determine that there is a difference in the beam energy of the first radiation beam and the second radiation beam. In some embodiments, the processor may determine maximum energy of the first energy spectrum and maximum energy of the second energy spectrum. If there is a difference between the maximum energy of the first radiation beam and the maximum energy of the second radiation beam, the processor may determine that there is a difference in the beam energy of the first radiation beam and the second radiation beam.

It should be noted that the diagnostic and treatment system 100 described below is merely provided for illustration purposes, and not intended to limit the scope of the present disclosure. For persons having ordinary skills in the art, a certain amount of variations, changes, and/or modifications may be deducted under the guidance of the present disclosure. Those variations, changes, and/or modifications do not depart from the scope of the present disclosure.

Figure 1:
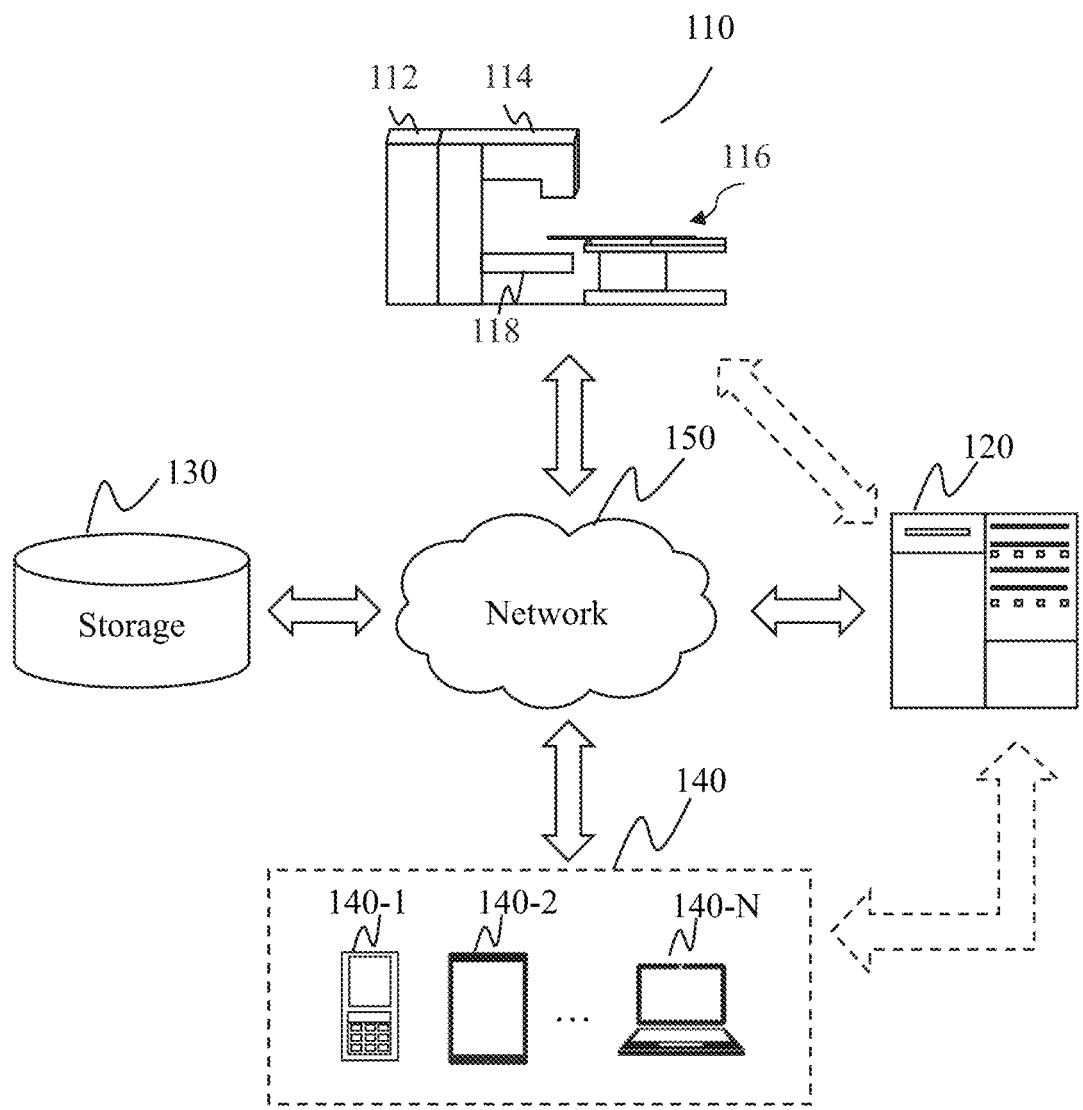
FIG. 1 is a schematic diagram illustrating an exemplary diagnostic and treatment system according to some embodiments of the present disclosure.

FIG. 1 is a schematic diagram illustrating an exemplary diagnostic and treatment system 100 according to some embodiments of the present disclosure. As shown, the diagnostic and treatment system 100 may include an RT device 110, a processing engine 120, a storage 130, one or more terminal(s) 140, and a network 150. In some embodiments, the RT device 110, the processing engine 120, the storage 130, and/or the terminal(s) 140 may be connected to and/or communicate with each other via a wireless connection (e.g., the network 150), a wired connection, or a combination thereof. The connections between the components in the diagnostic and treatment system 100 may vary. Merely by way of example, the RT device 110 may be connected to the processing engine 120 through the network 150, as illustrated in FIG. 1. As another example, the RT device 110 may be connected to the processing engine 120 directly. As a further example, the storage 130 may be connected to the processing engine 120 through the network 150, as illustrated in FIG. 1, or connected to the processing engine 120 directly. As still a further example, the terminal(s) 140 may be connected to the processing engine 120 through the network 150, as illustrated in FIG. 1, or connected to the processing engine 120 directly. In some embodiments, the RT device 110 may be a single-modality apparatus to deliver radiation therapy. In some embodiments, the RT device 110 may be a multi-modality (e.g., two-modality) apparatus to acquire a medical image relating to at least one part of a subject and perform radiotherapy on the at least one part of the subject. The medical image may be a computed tomography (CT) image, a magnetic resonance imaging (MRI) image, an ultrasonic image, or the like, or a combination thereof. In some embodiments, the medical image may be a two-dimensional (2D) image, a three-dimensional (3D) image, a four-dimensional (4D) image, or the like, or a combination thereof. The subject may be biological or non-biological. For example, the subject may include a patient, a man-made object, etc. As another example, the subject may include a specific portion, organ, and/or tissue of the patient. For example, the subject may include head, neck, thorax, cardiac, stomach, blood vessel, soft tissue, tumor, nodules, or the like, or a combination thereof. In some embodiments, the RT device 110 may include an imaging device 112, a treatment device 114, and a couch 116. The imaging device 112 may be configured to provide the medical image for determining the at least one part of the subject (e.g., an anatomical point). Exemplary imaging devices may include, for example, a CT device, a cone beam CT device, a PET device, a volume CT device, an MRI device, or the like, or a combination thereof. The treatment device 114 may be configured to perform radio therapy on the at least one part of the subject according to the medical image and other information. Exemplary treatment devices may include a linear accelerator, an X-rays treatment device, etc. In some embodiments, the imaging device 112 may include an imaging detector 118. The imaging detector 118 may be configured to detect a distribution of radiation beams. In some embodiments, the imaging detector 118 may be connected to a data conversation circuit configured to convert the distribution of the detected radiation beams into image data (e.g., projection data). The couch 116 may be configured to support and/or transfer the at least one part of the subject to for example, a scanning region of the imaging device 112 and/or the treatment device 114. For example, the couch 116 may be moved to transfer the at least one part of the subject from the imaging device 112 to the treatment device 114.

In some embodiments, the imaging device 112 and the treatment device 114 may be located separately from each other. In some embodiments, the imaging device 112 may be coupled with the treatment device 114. The imaging device 112 and the treatment device 114 may share a same bore which may be used to accommodate a subject to be imaged and/or treated. The couch 116 may be configured to transfer the subject to be imaged and/or treated to a detecting region in the bore. The couch 116 may include a movement assembly configured to move the couch 116 along various directions. For example, the movement assembly may extend the couch 116 along the longitudinal direction of the couch 116. As another example, the movement assembly may lift the couch 116 in the vertical direction.

The processing engine 120 may process data and/or information obtained from the RT device 110, the storage 130, and/or the terminal(s) 140. For example, the processing engine 120 may reconstruct an image relating to at least one part of a subject (e.g., a tumor) based on projection data collected by the RT device 110 (e.g., the imaging device 112). As another example, the processing engine 120 may determine a treatment plan based on at least one part of a subject (e.g., a tumor) represented in an image acquired by the imaging device 112.

In some embodiments, the processing engine 120 may be a single server or a server group. The server group may be centralized or distributed. In some embodiments, the processing engine 120 may be local or remote. For example, the processing engine 120 may access information and/or data from the RT device 110, the storage 130, and/or the terminal(s) 140 via the network 150. As another example, the processing engine 120 may be directly connected to the RT device 110, the terminal(s) 140, and/or the storage 130 to access information and/or data. In some embodiments, the processing engine 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing engine 120 may be implemented by a mobile device 300 having one or more components as described in connection with FIG. 3.

The storage 130 may store data, instructions, and/or any other information. In some embodiments, the storage 130 may store data obtained from the RT device 110, the processing engine 120, and/or the terminal(s) 140. In some embodiments, the storage 130 may store data and/or instructions that the processing engine 120 may execute or use to perform exemplary methods described in the present disclosure. In some embodiments, the storage 130 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 130 may be implemented on a cloud platform as described elsewhere in the disclosure.

In some embodiments, the storage 130 may be connected to the network 150 to communicate with one or more other components in the diagnostic and treatment system 100 (e.g., the processing engine 120, the terminal(s) 140, etc.). One or more components in the diagnostic and treatment system 100 may access the data or instructions stored in the storage 130 via the network 150. In some embodiments, the storage 130 may be part of the processing engine 120.

The terminal(s) 140 may be connected to and/or communicate with the RT device 110, the processing engine 120, and/or the storage 130. For example, the terminal(s) 140 may obtain a processed image from the processing engine 120. As another example, the terminal(s) 140 may obtain image data acquired via the RT device 110 and transmit the image data to the processing engine 120 to be processed. In some embodiments, the terminal(s) 140 may include a mobile device 140-1, a tablet computer 140-2, . . . , a laptop computer 140-N, or the like, or any combination thereof. For example, the mobile device 140-1 may include a mobile phone, a personal digital assistance (PDA), a gaming device, a navigation device, a point of sale (POS) device, a laptop, a tablet computer, a desktop, or the like, or any combination thereof. In some embodiments, the terminal(s) 140 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing engine 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing engine 120.

The network 150 may include any suitable network that can facilitate exchange of information and/or data for the diagnostic and treatment system 100. In some embodiments, one or more components of the diagnostic and treatment system 100 (e.g., the RT device 110, the processing engine 120, the storage 130, the terminal(s) 140, etc.) may communicate information and/or data with one or more other components of the diagnostic and treatment system 100 via the network 150. For example, the processing engine 120 may obtain image data from the RT device 110 via the network 150. As another example, the processing engine 120 may obtain user instruction(s) from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the diagnostic and treatment system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage 130 may be a data storage including cloud computing platforms, such as, public cloud, private cloud, community, and hybrid clouds, etc. However, those variations and modifications do not depart the scope of the present disclosure.

Figure 2:
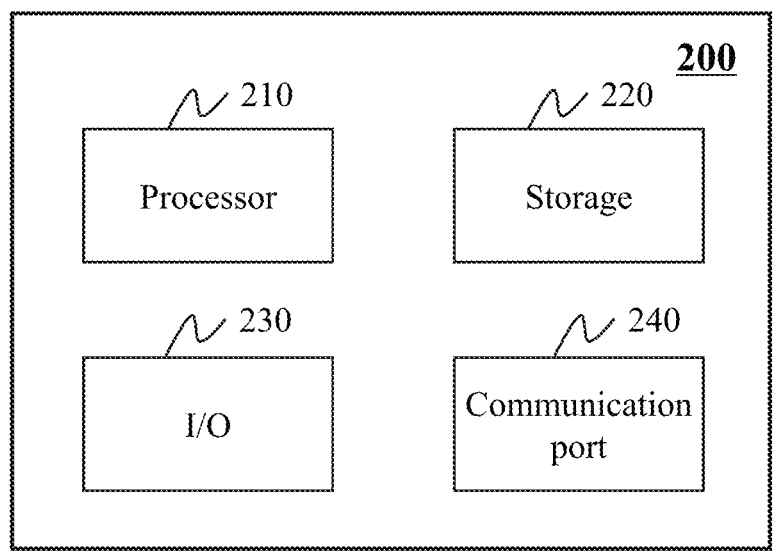
FIG. 2 is a schematic diagram illustrating exemplary hardware and/or software components of an exemplary computing device according to some embodiments of the present disclosure.

FIG. 2 is a schematic diagram illustrating exemplary hardware and/or software components of an exemplary computing device 200 on which the processing engine 120 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing engine 120 in accordance with techniques described herein. The computer instructions may include, for example, routines, programs, objects, components, data structures, procedures, modules, and functions, which perform particular functions described herein. For example, the processor 210 may process image data obtained from the RT device 110, the storage 130, terminal(s) 140, and/or any other component of the diagnostic and treatment system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the RT device 110, the storage 130, the terminal(s) 140, and/or any other component of the diagnostic and treatment system 100. In some embodiments, the storage 220 may include a mass storage, a removable storage, a volatile read-and-write memory, a read-only memory (ROM), or the like, or a combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing engine 120 for determining a target flip angle schedule.

The I/O 230 may input and/or output signals, data, information, etc. In some embodiments, the I/O 230 may enable a user interaction with the processing engine 120. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing engine 120 and the RT device 110, the storage 130, and/or the terminal(s) 140. The connection may be a wired connection, a wireless connection, any other communication connection that can enable data transmission and/or reception, and/or a combination of these connections. The wired connection may include, for example, an electrical cable, an optical cable, a telephone wire, or the like, or a combination thereof. The wireless connection may include, for example, a Bluetooth™ link, a Wi-Fi™ link, a WMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device 300 on which the terminal(s) 140 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing engine 120. User interactions with the information stream may be achieved via the I/O 350 and provided to the processing engine 120 and/or other components of the diagnostic and treatment system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
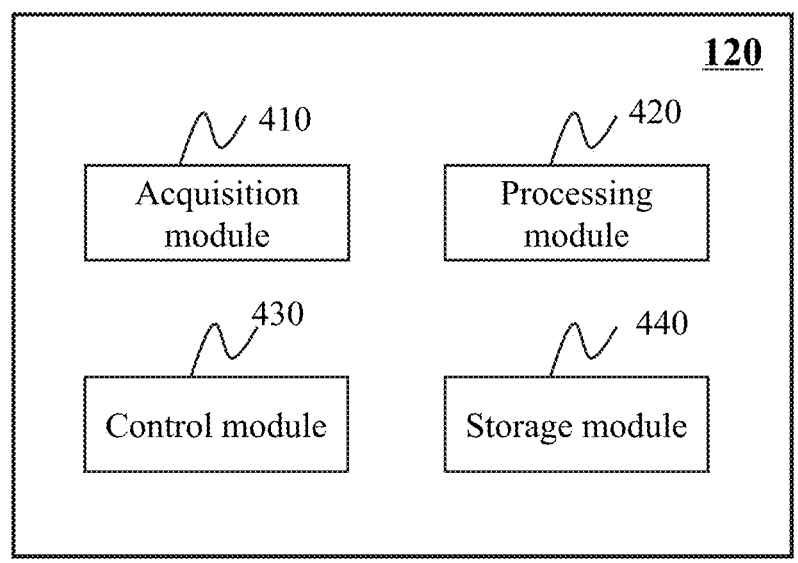
FIG. 4 is a block diagram illustrating an exemplary processing engine according to some embodiments of the present disclosure.

FIG. 4 is a block diagram illustrating an exemplary processing engine 120 according to some embodiments of the present disclosure. The processing engine 120 may include an acquisition module 410, a processing module 420, a control module 430, and a storage module 440. The modules may be hardware circuits of at least part of the processing engine 120. The modules may also be implemented as an application or set of instructions read and executed by the processing engine 120. Further, the modules may be any combination of the hardware circuits and the application/instructions. For example, the modules may be the part of the processing engine 120 when the processing engine 120 is executing the application/set of instructions.

The acquisition module 410 may acquire data from one or more components of the diagnostic and treatment system 100 (e.g., the RT device 110, the processing engine 120, the storage 130 and the terminal(s) 140.). In some embodiments, the acquisition module 410 may acquire a treatment plan from the storage 130. In some embodiments, the acquisition module 410 may acquire a signal generated by a first dosimeter or a second dosimeter of the RT device 110 upon receiving a radiation beam. In some embodiments, the signal may be related to a radiation output rate and/or an energy spectrum of the radiation beam. The radiation beam may include a first radiation beam generated at a first time point and a second radiation beam generated at a second time point. The first radiation beam and the second radiation beam may be used for imaging or treatment. For example, the first radiation beam may be generated under a first mode (e.g., a treatment mode), and the second radiation beam may be generated under a second mode (e.g., an imaging mode or a calibration mode, etc.). A radiation beam generated under the imaging mode may target at least a part of the subject and may be used to generate a medical image before a treatment, during a treatment or after a treatment. A radiation beam generated under the treatment mode may be intended for treatment towards the ROI.

In some embodiments, the acquisition module 410 may acquire a first signal and a third signal both generated by a first dosimeter. The first signal may correspond to a first radiation output rate of the first radiation beam, and the third signal may correspond to a third radiation output rate of a second radiation beam. The acquisition module 410 may also acquire a second signal and a fourth signal both generated by a second dosimeter. The second signal may correspond to at least one of a second radiation output rate of the first radiation beam or a first energy spectrum of the first radiation beam, and the fourth signal corresponds to at least one of a fourth radiation output rate of the second radiation beam or a second energy spectrum of the second radiation beam. In some embodiments, the acquisition module 410 may transmit the acquired data to the processing module 420.

The processing module 420 may process data related to one or more components of the diagnostic and treatment system 100 (e.g., the RT device 110, the processing engine 120, the storage 130 and the terminal(s) 140.). For example, the processing module 420 may determine a radiation output rate or determine whether there is a change in beam energy. For example, the processing module 420 may determine whether there is a difference in the beam energy of two radiation beams generated at different time points. The processing module 420 may determine a first relationship between the first signal generated by a first dosimeter and the second signal generated by a second dosimeter. The first signal and the second signal may correspond to a first radiation beam generated at a first time point. The processing module 420 may determine a second relationship between a third signal generated by the first dosimeter and a fourth signal generated by the second dosimeter. The third signal and the fourth signal may correspond to a second radiation beam generated at a second time point. If there is a difference in the first relationship and the second relationship, the processing module 420 may determine that there is a difference between the beam energy of the first radiation beam and the second radiation beam. In some embodiments, the processing module 420 may determine the energy spectrum of a scattered radiation beam based on Compton scatter spectroscopy (as will be describe in connection to FIG. 7). The processing module 420 may determine whether there is a difference in the maximum energy (e.g., the peak energy) of a first energy spectrum of the first radiation beam and a second energy spectrum of the second radiation beam. If there is the difference between the maximum energy of the first energy spectrum and the maximum energy of the second energy spectrum, the processing module 420 may determine that there is a change in the beam energy of the first radiation beam and the beam energy of the second radiation beam.

The control module 430 may be used to generate a control signal to the one or more components of the diagnostic and treatment system 100 (e.g., the RT device 110, the processing engine 120, the storage 130 and the terminal(s) 140.). For example, the control module 430 may send an instruction to the RT device 110 and initiate an imaging process or a treatment process. As another example, the control module 430 may send an instruction to direct the processing module 420 to determine whether there is a change in the beam energy. In some embodiments, the instruction may be input by a user (e.g., a doctor) via a user interface in the terminal(s) 140.

The storage module 440 may be used to store data related to the one or more components of the diagnostic and treatment system 100 (e.g., the RT device 110, the processing engine 120, the storage 130 and the terminal(s) 140.).

For example, the storage module 440 may store the energy spectrum determined by the processing module 430. As another example, the change in the beam energy (if any) may also be stored by the storage module 440 for a future analysis.

It should be noted that the above description of the processing engine 120 is merely provided for the purposes of illustration, and not intended to limit the scope of the present disclosure. For persons having ordinary skills in the art, multiple variations and modifications may be made under the teachings of the present disclosure. For example, the processing engine 120 may further include a communication module to facilitate data communications. However, those variations and modifications do not depart from the scope of the present disclosure.

FIGS. 5A to 5D are schematic diagrams illustrating an exemplary treatment head 500 of the radiation therapy device 110 according to some embodiments of the present disclosure. The treatment head 500 may include a radiation source 501, a primary collimator 502, a first dosimeter 504, a backscatter plate 505, a secondary collimator 507, and a second dosimeter 510.

The radiation source 501 may include a particle generator, an accelerating tube, and a target. The particle generator may be configured to generate charged particles such as electrons. The accelerating tube may be configured to accelerate the charged particles to obtain a high-speed particle beam. The high-speed particle beam may hit the target to generate a radiation beam 512. For example, the target may be made of tungsten. The radiation beam 512 may include a particle beam (e.g., a neutron beam, a proton beam, an electron beam, etc.), a photon beam (e.g., an X-ray, a γ-ray), or the like, or a combination thereof. In some embodiments, the radiation beam 512 may be an imaging beam or a treatment beam. In some embodiments, the radiation output rate of the imaging beam may be lower than the radiation output rate of the treatment beam.

Figure 5A:
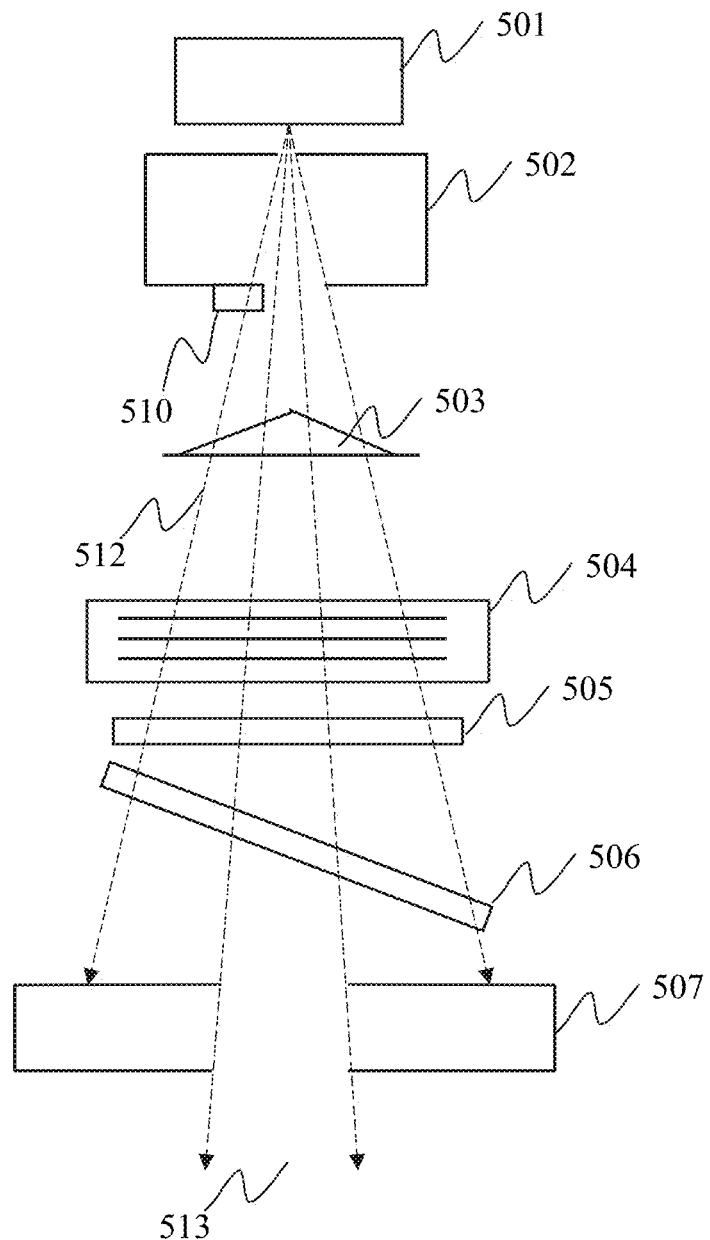
FIGS. 5A to 5D are schematic diagrams illustrating an exemplary treating head of a diagnostic and treatment device according to some embodiments of the present disclosure.
Figure 5B:
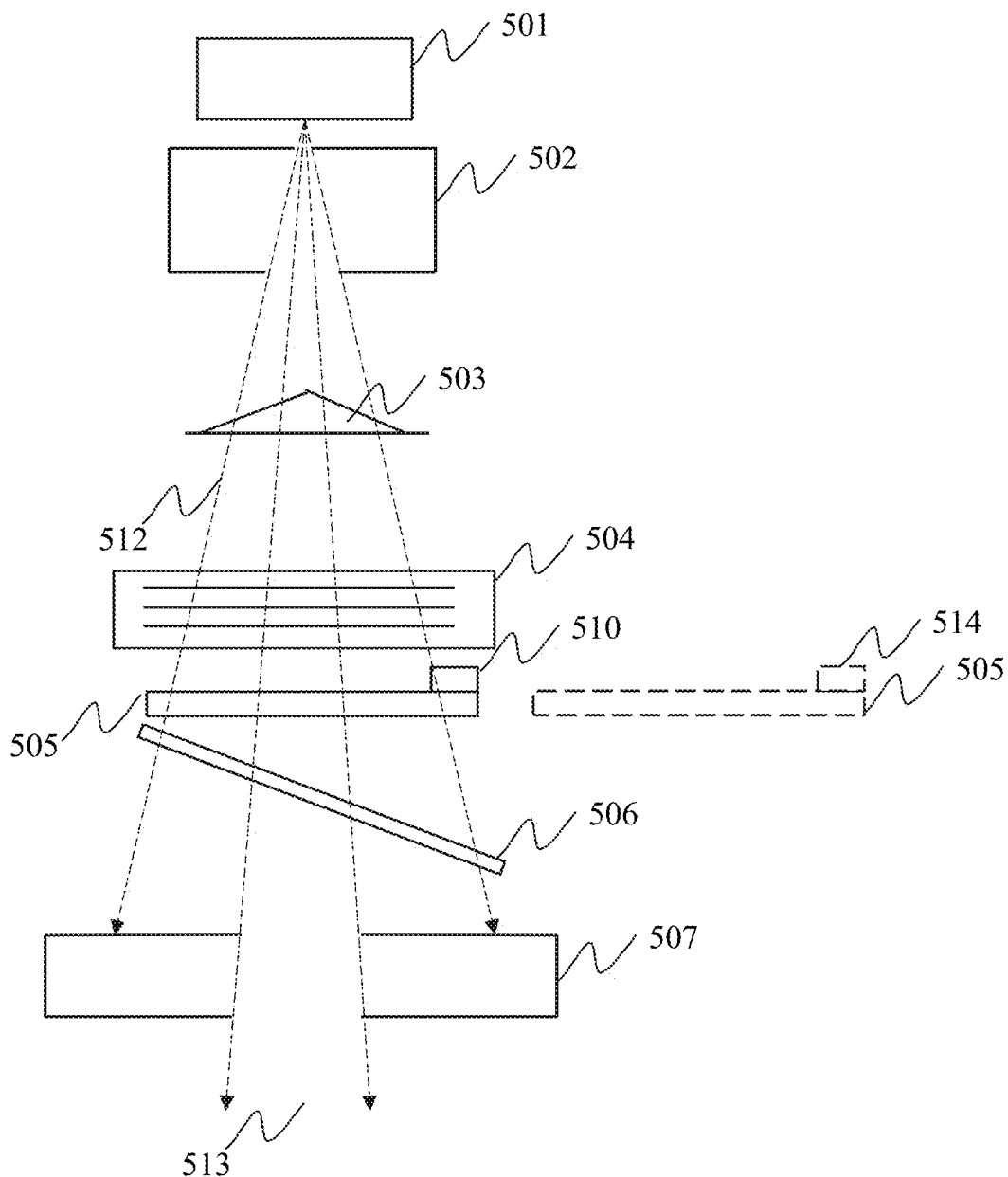

The primary collimator 502 may be configured to delimit an extent of the radiation beam 512 and define a maximum size for a radiation-beam-passing-through area 513. As used herein, a radiation-beam-passing-through area 513 may refer to an area traversed by the radiation beam 512 after the radiation beam 512 is emitted out of a second collimator 507 as illustrated in FIG. 5A. In some embodiments, the primary collimator 502 may include a block made of high attenuation material and may be positioned dose to the radiation source 501. The high attenuation material may be, for example, lead, depleted uranium, tungsten, etc. At least portion of the radiation beam 512 may be blocked by the primary collimator 502 and thus the radiation beam 512 may be shaped by the primary collimator 502.

The first dosimeter 504 may be configured to detect the radiation output rate of the radiation beam 512. In some embodiments, the first dosimeter 504 may generate a first signal corresponding to the radiation output rate of a first radiation beam upon receiving at least portion of the first radiation beam. The first radiation beam may be generated at a first time point. In some embodiments, the first radiation beam may be generated at the first time point under a first mode (e.g., a treatment mode). The first radiation beam generated under the treatment mode may be intended for treatment towards the ROI of the subject. The first dosimeter 504 may generate a third signal corresponding to the radiation output rate of a second radiation beam upon receiving at least portion of the first radiation beam. The second radiation beam may be generated at a second time point. In some embodiments, the second radiation beam may be generated at the second time point under a second mode (e.g., an imaging mode, a calibration mode, etc.). The second radiation beam generated under the imaging mode may be intended for acquiring images of the ROI of the subject. The second radiation beam generated under the calibration mode may be intended for calibration purposes. In some embodiments, the energy level of the second radiation beam generated in the second mode may be lower than the energy level of the first radiation beam generated in the first mode. In some embodiments, the first radiation beam generated at the first time point and the second radiation beam generated at the second time point may be generated under a same mode.

In some embodiments, the first dosimeter 504 may include an ionization chamber. The ionization chamber may be designed to pass as much radiation as possible so as not to significantly reduce an intensity of the radiation beam 512 or cause scatter of the radiation beam 512. Thus the ionization chamber may exhibit low quantum efficiency. The ionization chamber may include a gas ionization chamber, a liquid ionization chamber, a solid ionization chamber, etc. In some embodiments, the ionization chamber may be coupled to a charge amplifier. Upon receiving radiation, a current may be generated in a circuit connected to the ionization chamber. The charge amplifier may be configured to produce a voltage output proportional to an integrated value of the current. The current may be determined based on a measurement of the voltage output and a correlation between the voltage output and the current.

Many RT systems include a backscatter plate (e.g., the backscatter plate 505) distal along a beam path to the primary dosimeter 504. The backscatter plate 505 may be configured to prevent the backscattered radiation from the secondary collimator 507 from reaching the first dosimeter 504. This may improve accuracy of the first dosimeter 504. In some embodiments, the backscatter plate 505 may be designed to move in and out of the radiation beam 512. The backscatter plate 505 may be positioned between the first dosimeter 504 and the secondary collimator 507.

The secondary collimator 507 may be configured to shape the radiation beam 512 to conform to a shape of a region of interest (ROI) to be scanned and/or to be treated. The ROI may include an organ (e.g., a breast, a lung, a liver, etc.), a tumor, injured tissue, calcified tissue, or the like, or any combination thereof. In some embodiments, the secondary collimator 507 may include a plurality of jaws. The plurality of jaws may be blocks used to shape the radiation beam 512. In some embodiments, the secondary collimator 507 may include a multi-leaf collimator (MLC). The MLC may include individual leaves that may independently move in and out of the path of the radiation beam 512 in order to block portion of the radiation beam 512. The MLC may provide highly conformal shaping of the radiation beam 512.

The second dosimeter 510 may be configured to detect the radiation output rate and/or the energy spectrum of the radiation beam 512. In some embodiments, the combined information output by the first dosimeter 504 and the second dosimeter 510 may be configured to detect changes in beam energy based on the differential energy response of the first dosimeter 504 and the second dosimeter 510. Alternatively or additionally, the second dosimeter 510 may be configured to monitor the beam energy of the second radiation beam based on Compton scatter spectroscopy as described in connection with FIG. 7.

In some embodiments, the second dosimeter 510 may generate a second signal corresponding to the radiation output rate and/or the energy spectrum of the first radiation beam upon receiving at least portion of the first radiation beam. The second dosimeter 510 may generate a fourth signal corresponding to the radiation output rate of the second radiation beam upon receiving at least portion of the second radiation beam. In some embodiments, the first radiation beam and the second radiation beam may be generated under a same mode or different modes. Exemplary modes may include a treatment mode, an imaging mode, a calibration mode, etc. In some embodiments, the quantum efficiency of the second dosimeter 510 may be higher than the quantum efficiency of the first dosimeter 504, especially within the energy range of an imaging beam. Merely as an example, if the first radiation beam (e.g., a treatment beam) has a peak energy of 6 MeV, and the second radiation beam (e.g., an imaging beam) has a peak energy of 3.5 MeV, there would be advantages in the second dosimeter having higher quantum efficiency for measuring the second radiation beam.

In some embodiments, the second dosimeter 510 may include an optical detector and a scintillator connected to the optical detector. The scintillator may be configured to receive direct or scattered particle radiation and emit photons. The optical detector may detect the photons emitted by the scintillator, or photons from a photon beam, and re-emit electrons via a photoelectric effect. In some embodiments, a light guide such as an optic fiber may be used to allow the optical detector to be placed in a location that is shielded from radiation and/or further from the beam, beam scatter and neutrons created by the beam. The optical detector may be connected to the light guide to allow the photons to reach a sensitive part of the optical detector. In some embodiments, the optical detector may be an optical semiconductor. For example, the optical detector may include a photodiode. The photodiode may convert the light into an electrical current for measurement. In some embodiments, the scintillator may be a phosphor, such as a $Gd_2O_2S$ phosphor or a CsI phosphor. In some embodiments, the optical detector may include a photomultiplier and the scintillator may include a cadmium telluride scintillator. The photomultiplier may be highly sensitive to the light and may multiply the current produced by the light. Such an optical detector may be able to measure energy of individual photons/particles incident on the optical detector. In some embodiments, more than one optical detector may be used. Each of the more than one optical detector may be coupled to a phosphor assembly that exhibits a different spectral response. Thus the second dosimeter 510 may exhibit a dynamic range of several orders of magnitude. For example, two or more photodiodes may be couple to a phosphor assembly with different phosphor thicknesses or different shields from the radiation beam 512. In some embodiments, the second dosimeter 510 may be more sensitive to the radiation than the first dosimeter 504 when the quantum efficiency of the second dosimeter 510 is higher than the first dosimeter 504. For example, when the second dosimeter 510 and the first dosimeter 504 receive a same amount of radiation output, the second dosimeter 510 may generate a higher current than the first dosimeter 504. This may be especially the case when the imaging beam exhibits a generally lower energy spectrum than the treatment beam.

Figure 5C:
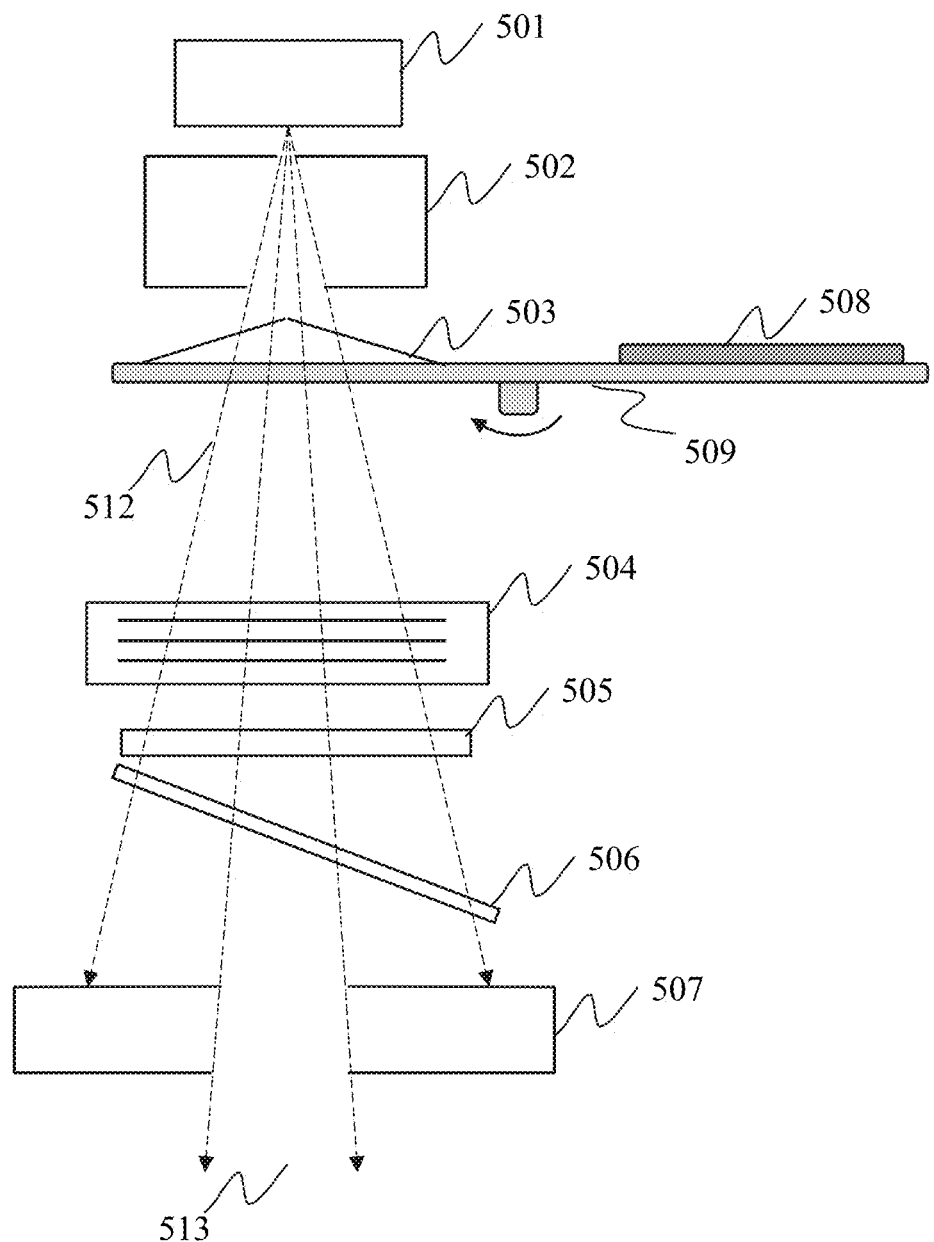

In some embodiments, the second dosimeter 510 may be positioned to receive primary radiation while not blocking any portion of the radiation-beam-passing-through area 513. As used herein, "primary radiation" may refer to radiation directly from the radiation source 501 without any scattering, i.e., radiation that travels continuously in substantially straight rays from the source, in a substantially constant direction. For example, the second dosimeter 510 may be positioned between the primary collimator 502 and the first dosimeter 504 as illustrated in FIG. 5A. As another example, the second dosimeter 510 may be positioned between the radiation source 501 and the primary collimator 502. As yet another example, the second dosimeter 510 may be positioned inside the primary collimator 502. As still another example, the second dosimeter 510 may be positioned on the backscattered plate 505 that protrudes into the radiation beam 512 as illustrated by an exemplary second dosimeter 514 in FIG. 5B. In some embodiments, the position of the second dosimeter 510 may be adjusted to allow the second dosimeter 510 to move in or out of the radiation beam 512 to receive primary or scattered radiation, respectively. Prolonged exposure to the first radiation beam with relatively high radiation output, i.e., a treatment beam, may reduce lifespan of the second dosimeter 510. A much longer lifespan may be expected if the second dosimeter 510 is only exposed to the direct beam during the second radiation beam with relatively low radiation output, i.e., an imaging beam. In some embodiments, the second dosimeter 510 may be located on a moveable component, such as a carousel, a backscattered plate, or any other moveable supporter. The carousel may be used for switching a component to be in and out of the radiation beam 512. For instance, the carousel may be a carousel 509 for switching the flattening filter 503 or a scattering foil 508 as illustrated in FIG. 5C. The dosimeter 510 may be located in a cavity of the carousel 509 and may be moved in and out of the radiation beam 512 as required. Alternatively, the carousel may be used for switching the primary collimator 502 as described in connection with FIG. 6. In some embodiments, there may be a plurality of primary collimators 502 designed specifically, for example, for different field sizes. The carousel may switch the positions of the plurality of primary collimators 502 for locating an appropriate primary collimator in the radiation beam 512. The dosimeter 510 may be located inside the wall of one of a plurality of primary collimators 502 in a cavity of the carousel, such as a primary collimator 502 for imaging beamlines. In some embodiments, the dosimeter 510 may be positioned on the backscattered plate 505. The backscatter plate 505 may move in and out of the radiation beam 512. The carousel or the backscatter plate 505 may enable the second dosimeter 510 to move into the radiation beam 512 for receiving direct radiation, or move the second dosimeter 510 out of the radiation beam 512 for receiving scattered radiation as required. In some embodiments, the second dosimeter 510 may be placed out of the radiation beam 512 to receive scattered radiation from both the treatment beam and the imaging beam. For example, the second dosimeter 510 may be positioned inside the primary collimator 502 without the carousel to receive scattered radiation. As another example, one or more blocks may be positioned in the radiation beam 512 without blocking any portion of the radiation-beam-passing-through area 513. The second dosimeter 510 may be placed out of the radiation beam 512 and receive radiation scattered by the one or more blocks from a first angle (as will be illustrated in FIG. 5D).

In some embodiments, the treatment head 500 may further include a flattening filter 503. The flattening filter 503 may be configured to make intensity of a photon beam to be uniform. The flattening filter 503 may be located between the primary collimator 502 and the first dosimeter 504. In some embodiments, as illustrated in FIG. 5C, the flattening filter 503 may be located on the carousel 509. A scattering foil 508 may also be located on the carousel 509. When a particle beam (e.g., an electron beam) hits the scattering foil 508, the particle beam may be spread to a wider area and get more uniform fluence. The carousel 509 may move the flattening filter 503 out of the radiation beam 512 and place the scattering foil 508 in the radiation beam 512 via rotation. A selection between the flattening filter 503 and the scattering foil 508 may be determined based on a radiation type of the radiation beam 512. For example, if the radiation beam 512 is a photon beam, the flattening filter 503 may be selected; and if the radiation beam 512 is a particle beam, the scattering foil 508 may be selected. In some embodiments, the treatment head 500 may be used under a flattening-filter-free (FFF) mode. FFF beams may provide a higher dose rate and may be used in limited, small field sizes, for example, in TomoTherapy® and CyberKnife® machines.

In some embodiments, the treatment head 500 may further include a mirror 506. The mirror 506 may be configured to facilitate a visual observation of the radiation-beam-passing-through area 513. The mirror 506 may be placed between the backscatter plate 505 and the secondary collimator 507. In some embodiments, the mirror may be 45 degrees to a central axis of the radiation beam 512. A light beam that is perpendicular to the central axis of the radiation beam 512 may be reflected by the mirror 506 in a same direction as the radiation beam 512. Then the reflected light beam may be shaped by the secondary collimator 507, and thus the reflected light beam coming out of the collimator 507 may have the same shape as the radiation beam 512. In some embodiments, the light beam may be colored. A user (e.g., a doctor) may compare a conformability of the radiation beam 512 and the ROI by comparing the shape of the reflected light beam and the shape of the ROI. This may be a verification step or a safety insurance step during an imaging process or a radiation treatment. In some embodiments, the reflected light beam may assist in positioning the subject (e.g., a patient) on a couch.

Figure 5D:
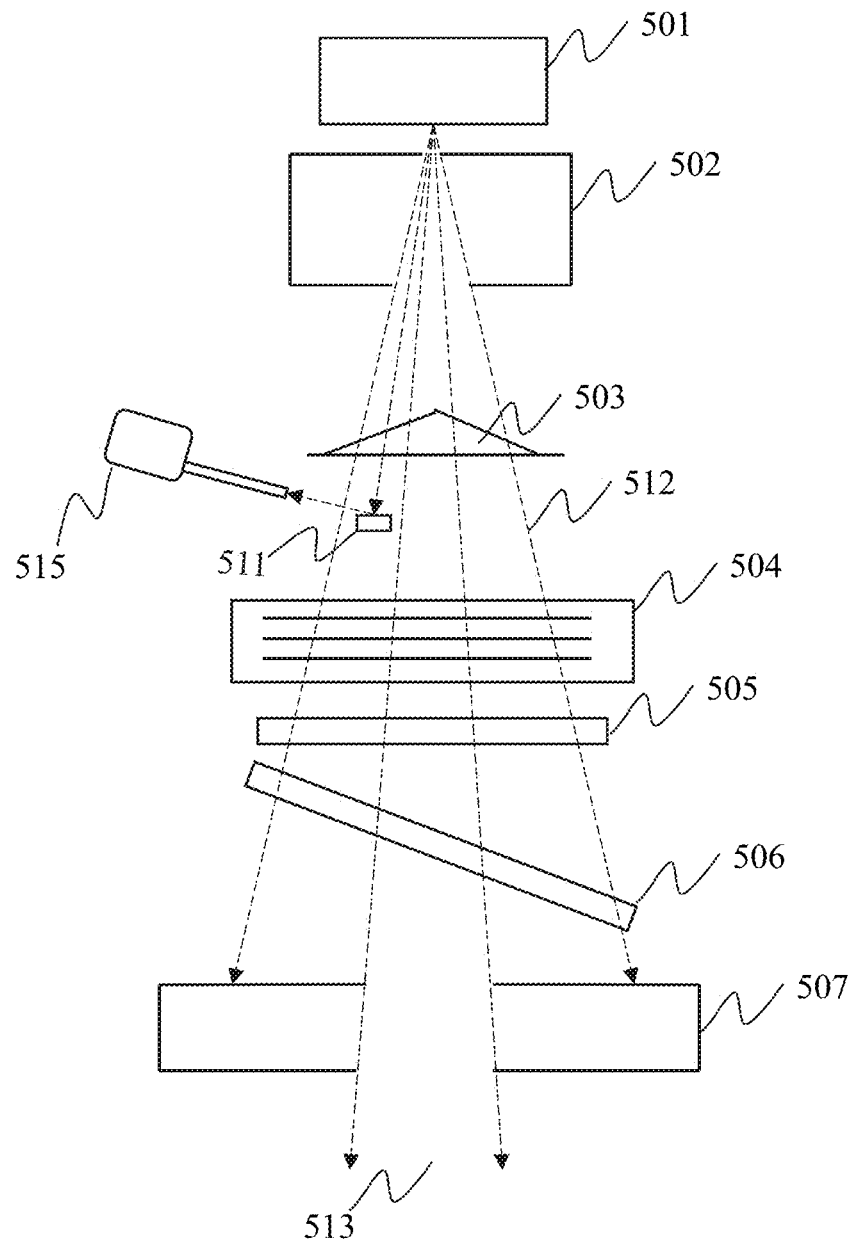

In some embodiments, the secondary dosimeter 510 may detect a beam spectrum by using a method based on Compton scatter spectroscopy. The method based on Compton scatter spectroscopy utilizes a scattering block to reduce photon flux and preventing pulse pile up and dosimeter saturation or damage. As used herein, "pulse pile up" may refer to an effect of falsely counting multiple photons as one photon with accumulated energy by a dosimeter. For example, as illustrated in FIG. 5D, a block 511 may be positioned between the primary collimator 502 and the secondary collimator 507 without blocking any portion of the radiation-beam-passing-through area 513. The second dosimeter 510 (as illustrated by an exemplary second dosimeter 515 in FIG. 5D) may receive at least portion of the radiation beam 512 scattered from the block 511 at a first angle. Exemplary first angles may include seventy degrees, eighty degrees, ninety degrees, etc. A suitable material for the block 511 may include methyl methacrylate (PMMA). In some embodiments, multiple blocks 511 may be positioned to decrease an amount of photons and/or particles incident on the secondary dosimeter 510. In some embodiments, a suitable material for the optical detector of the secondary dosimeter 510 may include high purity germanium (HPGe). The secondary dosimeter 510 may be coupled to a long and narrow collimator so that it is possible to count photons that arrive at the optical detector, and to decrease incident scattered radiation. The secondary dosimeter 510 may detect maximum energy of scattered radiation beams generated at different time points. The processing engine 120 may determine whether there is a change in the beam energy by comparing the maximum energy of the scattered radiation beams generated at the different time points. For example, if the maximum energy of the scattered radiation beams generated at a first time point is different from the maximum energy of the scattered radiation beams generated at a second time point, the processing engine 120 may determine that there is a change in the beam energy. The processing engine 120 may evaluate, based on the change in the beam energy, system robustness, a system error, etc. This may be desirable for improving system safety or used for calibration.

It should be noted that the examples illustrated in FIGS. 5A to 5D and the above descriptions thereof are merely provided for the purposes of illustration, and not intended to limit the scope of the present disclosure. For persons having ordinary skills in the art, multiple variations or modifications may be made under the teachings of the present disclosure. For example, the treatment head 500 may include one or more additional components. As another example, one or more described components may be removed from the treatment head 500. However, those variations and modifications do not depart from the scope of the present disclosure.

Figure 6:
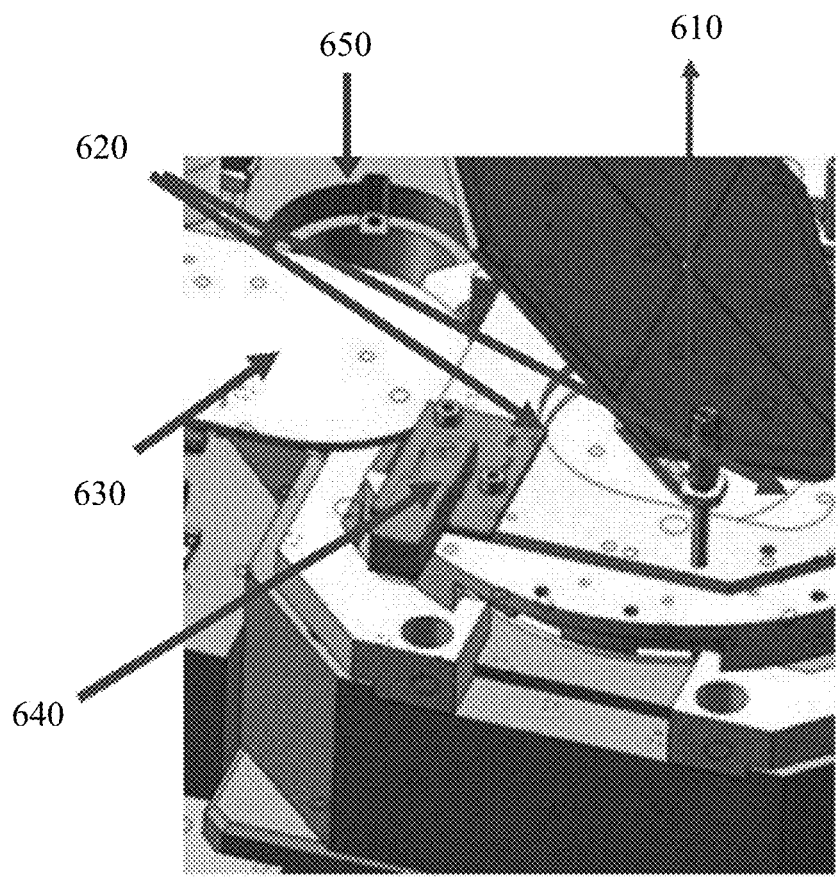
FIG. 6 is a schematic diagram illustrating an exemplary position of a second dosimeter according to some embodiments of the present disclosure.

FIG. 6 is a schematic diagram illustrating an exemplary position of a second dosimeter according to some embodiments of the present disclosure. As illustrated in FIG. 6, 610 may represent a central beam axis and direction. 620 may represent a beam port. When the beam port 620 is open, the radiation beam 512 may be emitted via the beam port 620. 630 may represent a backscatter plate. A sensor assembly 640 may be configured to monitor environmental conditions, such as the temperature and the humidity. For example, the sensor assembly 640 may include a temperature sensor, a humidity sensor, or the like, or any combination thereof. 650 may represent a primary collimator used for imaging beamlines (IBL) located in a carousel system. In some embodiments, a plurality of different primary collimators may be located in the carousel system. For example, the plurality of different primary collimators may include the primary collimator used for IBL and a primary collimator used for treatment beamlines (TBL). The primary collimator used for IBL may define a relatively large field size and a primary collimator used for TBL may define a relatively small field size. The carousel system may be adjusted to allow the radiation beam 512 to traverse a primary collimator as required. In some embodiments, the second dosimeter 510 may be positioned to receive primary radiation while not blocking any portion of the radiation-beam-passing-through area 513. In some embodiments, the second dosimeter 510 may be placed out of the radiation beam 512 to receive scattered radiation from both the first radiation beam, i.e., the treatment beam, and the second radiation beam, i.e., the imaging beam. For example, a second dosimeter 510 may be positioned adjacent to the beam port 620 or the sensor assembly 640 as illustrated in FIG. 6. At such a location, the second dosimeter 510 may measure scattered radiation from both treatment and image beams. As another example, the dosimeter 510 may be positioned by a side of the primary collimator for IBL 650 located in a cavity of the carousel system for the primary collimator 502. Thus the dosimeter 510 may measure the IBL dose. As yet another example, the second dosimeter 510 may be positioned on a leading edge of the backscatter plate 630. Thus a position of the second dosimeter 510 may be adjusted by moving the backscatter plate 630. For example, the second dosimeter 510 may protrude into portion of the radiation beam 512 when the radiation beam 512 is used for an imaging process, and stay out of the radiation beam 512 when the radiation beam 512 is used for a treatment process. As a result, the second dosimeter 510 may receive scattered radiation of the treatment beam and primary radiation of the imaging beam. In some embodiments, the second dosimeter 510 may receive scattered radiation for detecting the radiation output rate and/or the energy spectrum. The second dosimeter 510 may also be configured to monitoring beam energy changes for a treatment beam or an imaging beam.

FIG. 7 is a flowchart illustrating an exemplary process 700 for measuring a radiation output rate and monitoring beam energy according to some embodiments of the present disclosure. In some embodiments, one or more operations of the process 700 illustrated in FIG. 7 may be implemented in the diagnostic and treatment system 100 illustrated in FIG. 1. For example, at least a part of the process 700 illustrated in FIG. 7 may be stored in the storage 130 in the form of instructions, and invoked and/or executed by the processing engine 120 (e.g., the processor 210 of the computing device 200 as illustrated in FIG. 2, the GPU 330 or CPU 340 of the mobile device 300 as illustrated in FIG. 3).

In 702, the processing engine 120 may receive a first signal generated by a first dosimeter, the first signal corresponding to a first radiation output rate of a first radiation beam, wherein the first radiation beam is generated at a first time point by a radiation source.

In 704, the processing engine 120 may receive a third signal generated by the first dosimeter, the third signal corresponding to a third radiation output rate of a second radiation beam, wherein the second radiation beam is generated at a second time point by the radiation source.

In 706, the processing engine 120 may receive a second signal generated by a second dosimeter, the second signal corresponding to at least one of a second radiation output rate of the first radiation beam or a first energy spectrum of the first radiation beam.

In 708, the processing engine 120 may receive a fourth signal generated by the second dosimeter, the fourth signal corresponding to at least one of a fourth radiation output rate of the second radiation beam or a second energy spectrum of the second radiation beam.

In some embodiments, the first radiation beam generated at the first time point and the second radiation beam generated at the second time point may be generated under a same mode or different modes. An exemplary mode may include a treatment mode, an imaging mode, a calibration mode, etc. In some embodiments, the first radiation beam and the second radiation beam may be imaging beams. The imaging beam may target at least a part of the subject and may be used to generate a medical image before a treatment, during a treatment or after a treatment. The subject may be biological or non-biological, such as a patient, an animal, a man-made phantom, or the like. Knowledge of the radiation output per imaging frame may be important both for recording an imaging dose and for the normalization of an image intensity to the radiation output for the imaging. This may be particularly important for a cone beam CT scanning, in which severe image artifacts may result if the projection images are produced by a variable and unknown amount of radiation per image. The medical image generated based on the imaging beam may provide diagnostic information of the ROI and/or position information of the ROI. The ROI may include an organ (e.g., a breast, a lung, a liver, etc.), a tumor, injured tissue, calcified tissue, or the like, or any combination thereof. In some embodiments, the first radiation beam and the second radiation beam may be treatment beams. A treatment beam may be used to kill cancerous cells, to prevent a reoccurrence of a tumor, or to treat other indications. Knowledge of the radiation output rate for the treatment beam is important for determining a dose delivered to the subject. In some embodiments, the first radiation beam and the second radiation beam may be used in a calibration operation. For example, the calibration operation may be performed to reduce a systematic error. Monitoring the beam energy may also assist in evaluating system robustness and improving system safety.

In some embodiments, the radiation output rate of an imaging beam may be significantly lower than radiation output rate of a treatment beam. In some embodiments, quantum efficiency of the first dosimeter 504 may be lower than the second dosimeter 510. Thus the first dosimeter 504 may be more suitable for measuring the radiation output rate of a radiation beam with relatively high energy (e.g., a treatment beam). Merely by way of example, the first dosimeter 504 may be a gas ionization chamber, a liquid ionization chamber, a solid ionization chamber, or the like. In some embodiments, the first dosimeter 504 may receive mainly primary radiation coming directly from the radiation source 510 without scattering. In some embodiments, the at least portion of the first radiation beam may be scattered from the first radiation beam and received by the first dosimeter 504. Upon receiving the at least portion of the first radiation beam, the first dosimeter 504 may generate a first signal. The first signal may be, for example, a current corresponding to a first radiation output rate of the first radiation beam. The third signal from the first dosimeter 504 may be, for example, a current corresponding to a third radiation output rate of the second radiation beam.

In some embodiments, the second dosimeter 510 may be more sensitive than the first dosimeter as described in connection to FIG. 5A. For example, compared with the first dosimeter 504, the second dosimeter 510 may have a stronger response to a radiation beam with relatively low energy (e.g., an imaging beam). Thus the second dosimeter 510 may be more suitable for detecting the radiation output rate of an imaging beam. Similarly, the second signal from the second dosimeter 510 may be, for example, a current corresponding to the second radiation output rate of the first radiation beam generated at the first time point. In some embodiments, a first energy spectrum of the first radiation beam may be determined based on the second signal. The fourth signal from the second dosimeter may be, for example, a current corresponding to the fourth radiation output rate of the second radiation beam. In some embodiments, a second energy spectrum may be determined based on the fourth signal. The second dosimeter 510 may generate the second signal or the fourth signal upon receiving at least portion of the primary radiation or scattered radiation of the first radiation beam or the second radiation beam, respectively. In some embodiments, the second dosimeter 510 may include an optical detector coupled to a scintillator. For example, the second dosimeter 510 may include a photodiode coupled to a phosphor, a photomultiplier coupled to a cadmium telluride scintillator, etc. In some embodiments, the second dosimeter 510 may include more than one optical detector, each being coupled to a phosphor assembly that exhibits a different spectral response. The second dosimeter 510 may exhibit a dynamic range of several orders of magnitude as to spectral response. And thus the second dosimeter 510 may detect the radiation output rate both for an imaging beam and for a treatment beam. In some embodiments, the second dosimeter 510 may only be exposed in the radiation beam 512 to receive primary radiation from the imaging beam. In some embodiments, the second dosimeter 510 may be positioned to receive scattered radiation for both the imaging beam and the treatment beam. To expand lifespan of the second dosimeter 510, the second dosimeter 510 may receive mainly scattered radiation.

In some embodiments, the second dosimeter 510 may measure the first energy spectrum of the first radiation beam or the second energy spectrum of the second radiation beam based on Compton scatter spectroscopy. Energy of the radiation beam may be non-uniform with varying intensities and/or energy levels. A use of a flattering filter or a scattering foil may be an effective way to make the beam intensity profile more uniform at a depth (e.g., 1~20 cm) within the object receiving the radiation dose. In some embodiments, the second dosimeter 510 may receive at least portion of the second radiation beam or the first radiation beam scattered from one or more blocks at a first angle. In some embodiments, the second dosimeter 510 may be coupled to a collimator to decrease photons incident on the second dosimeter 510. A change may occur in the energy spectrum due to a scattering process. A measured energy spectrum b may be further used for reconstructing an original spectrum x based on a following equation (1)

$$b(E')=\int_0^\infty A(E',E) \times (E) dE \qquad (1)$$

wherein x(E) denotes a number of original photons with energy E, b(E') denotes measured photons of energy E', A(E',E) denotes a probability of detecting a photon of energy E' if a photon of energy E originates form the radiation source 501. The equation (1) may be decomposed as a following equation (2)

$$b_i = \Sigma_{j=1}^N A_{ij} x_j, i=1,\ldots M \qquad (2)$$

and written in a matrix notation (3)

$$\vec{b} = A\vec{x} \qquad (3)$$

wherein the N and M denotes the number of energy bins. The $\vec{x}$ may be determined based on a Bayesian deconvolution method, a matrix inversion method, etc.

In 710, a processing engine 120 may determine whether there is a difference between the beam energy of the first radiation beam and the beam energy of the second radiation beam based on at least one of the first signal, the second signal, the third signal or the fourth signal.

Monitoring beam energy may assist in evaluating system robustness, a systematic error, etc. This may also be desirable for quality assurance or for improving system safety. In some embodiments, if there is an unknown change in the beam energy of two radiation beams generated at different time points, the measured radiation output rates may be inaccurate. In some embodiments, the processing engine 120 may determine a first relationship between the first signal detected by the first dosimeter 504 and the second signal detected by the second dosimeter 510. The first signal and the third signal may both correspond to the first radiation beam. The processing engine 120 may determine a second relationship between the third signal detected by the first dosimeter 504 and the fourth signal detected by the second dosimeter 510. The third signal and the fourth signal may both correspond to the second radiation beam. For example, the first relationship may be a ratio of the first signal to the second signal, and the second relationship may be a ratio of the third signal to the fourth signal. As another example, the first relationship may be a ratio of the second signal to the first signal, and the second relationship may be a ratio of the fourth signal to the third signal. A dosimeter may be related to a calibration factor, wherein the calibration factor may be used to calibrate the output of the dosimeter for determining a radiation output rate. The calibration factor may depend on the differential spectral response of the dosimeter and a beam spectrum. The calibrated output of the dosimeter may be ideally linear for a specific beam with constant beam energy. If the beam energy of the first radiation beam and the second radiation beam is unchanged, the first relationship and the second relationship should remain constant. If the processing engine 120 determines a difference in the first relationship and/or the second relationship, there may be a difference in the beam energy for the first radiation beam and/or the second radiation beam. For example, if the second radiation beam has higher beam energy than the first radiation beam, the ratio of the third radiation output rate to the fourth radiation output rate may be lower than the ratio of the first radiation output rate to the second radiation output rate. This may be at least partly due to the fact that the second dosimeter 510 has a stronger response to lower energies compared with the first dosimeter 504.

In some embodiments, the processing engine 120 may compare the first relationship (or the second relationship) with a reference value. The reference value may be associated with a configured level of beam energy (e.g., 2 MV, 6 MV, etc.) for the first radiation beam (or the second radiation beam). For example, the reference value may be a relationship between a signal generated by the first dosimeter 504 and a signal generated by the second dosimeter 510 upon pre-receiving a radiation beam with the configured level of beam energy. The level of beam energy may be measured accurately. If there is a difference between the reference value and the first relationship, the processing engine 120 may determine that there is a change in the beam energy. In some embodiments, if a difference is frequently detected between the reference value and the relationship between the signals generated by the first dosimeter 502 and the second dosimeter 510, the processing engine 120 may determine that there is a system error associated with the beam energy.

In some embodiments, the ability to measure a low radiation output rate (e.g., for an imaging beam) may be limited for the first dosimeter 504. The radiation output rates of the first radiation beam and the second radiation beam may be so low that the radiation output rates cannot be measured accurately by the first dosimeter 504. Therefore, in some embodiments, the processing engine 120 may determine whether there is a change in the beam energy of the first radiation beam and the second radiation beam based on the first energy spectrum and the second energy spectrum measured by the second dosimeter 510. In some embodiments, the second dosimeter 510 may measure the first energy spectrum and the second energy spectrum upon receiving primary radiation from the first radiation beam and the second radiation beam. In some embodiments, the second dosimeter 510 may measure the first energy spectrum and the second energy spectrum upon receiving scattered radiation from the first radiation beam and the second radiation beam by using a method based on the Compton scattering spectroscopy as described earlier in the present disclosure. The second dosimeter 510 may receive scattered radiation from one or more blocks 511 as described in connection to FIG. 5D. The maximum energy (e.g., the peak beam energy) from the scattered radiation may be used for detecting the change in beam energy. The processing engine 120 may compare the maximum energy of the first beam spectrum and the second beam spectrum. If a difference between the maximum energy of the first beam spectrum and the maximum energy of the second beam spectrum is determined, then a change in the beam energy of the first radiation beam and the second radiation beam is detected.

It will be apparent to those skilled in the art that various changes and modifications can be made in the present disclosure without departing from the spirit and scope of the disclosure. In this manner, the present disclosure may be intended to include such modifications and variations if the modifications and variations of the present disclosure are within the scope of the appended claims and the equivalents thereof.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.

NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

We claim:

1. A radiation treatment device, comprising:
    a radiation source configured to generate a first radiation beam in a first mode and a second radiation beam in a second mode, and the energy level of the second radiation beam being lower than the energy level of the first radiation beam;
    a first dosimeter configured to
        receive at least a portion of the first radiation beam under the first mode, and
        generate a first signal upon receiving at least a portion of the first radiation beam, the first signal indicating a first radiation output rate of the radiation source under the first mode; and
    a second dosimeter configured to
        receive at least a portion of the second radiation beam under the second mode, and
        generate a second signal upon receiving at least a portion of the second radiation beam, the second signal indicating a second radiation output rate of the radiation source under the second mode;
    wherein quantum efficiency of the first dosimeter is lower than quantum efficiency of the second dosimeter.

2. The radiation treatment device of claim 1, wherein the second dosimeter comprises one or more optical detectors and a scintillator assembly coupled to the one or more optical detectors.

3. The radiation treatment device of claim 2, wherein at least one of the one or more optical detectors includes a photodiode.

4. The radiation treatment device of claim 2, wherein the scintillator assembly includes a phosphor.

5. The radiation treatment device of claim 2, wherein the scintillator assembly includes a $Gd_2O_2S$ phosphor.

6. The radiation treatment device of claim 2, wherein at least one of the one or more optical detectors includes a photomultiplier, and the scintillator assembly includes a cadmium telluride scintillator.

7. The radiation treatment device of claim 6, wherein the photomultiplier includes a silicon photomultiplier.

8. The radiation treatment device of claim 1, wherein the radiation treatment device further comprises a collimator configured to delimit an extent of the first radiation beam or the second radiation beam.

9. The radiation treatment device of claim 8, wherein the second dosimeter is placed so as not to block a radiation-beam-passing-through area between the radiation source and the collimator.

10. The radiation treatment device of claim 8, wherein the second dosimeter is placed on a moveable component.

11. The radiation treatment device of claim 8, wherein the radiation treatment device further comprises a backscatter plate located distal, along the beam path, to the first dosimeter, and the second dosimeter is located on the backscatter plate.

12. The radiation treatment device of claim 8, wherein the radiation treatment device further comprises a carrousel located between the radiation source and the first dosimeter, and the second dosimeter is located on the carrousel.

13. The radiation treatment device of claim 1, wherein the at least a portion of the second radiation beam received by the second dosimeter is scattered from the second radiation beam.

14. The radiation treatment device of claim 13, wherein the at least a portion of the second radiation beam received by the second dosimeter is scattered by a block located beyond a radiation-beam-passing-through area from a first angle.

15. The radiation treatment device of claim 1, wherein
    the first dosimeter is further configured to receive at least a portion of the second radiation beam under the second mode; and
    the second dosimeter is further configured to receive at least a portion of the first radiation beam under the first mode.

16. The radiation treatment device of claim 1, wherein the first mode is a treatment mode.

17. The radiation treatment device of claim 1, wherein the second mode is an imaging mode or a calibration mode.

18. The radiation treatment device of claim 1, wherein the second mode is the same as the first mode.

19. The radiation treatment device of claim 2, wherein the one or more optical detectors exhibit different spectral responses.

20. The radiation treatment device of claim 8, wherein the second dosimeter is located inside the collimator.

* * * * *